United States Patent
Alagappan et al.

(10) Patent No.: US 10,165,961 B2
(45) Date of Patent: Jan. 1, 2019

(54) ADJUSTABLE HEAD COIL SYSTEMS AND METHODS FOR MAGNETIC RESONANCE IMAGING

(75) Inventors: Vijayanand Alagappan, Sydney (AU); Fraser Robb, Aurora, OH (US); Miguel Angel Navarro, II, Sheffield Village, OH (US); Craig William Culver, Neosho, WI (US); Victor Taracila, Beachwood, OH (US); John Edward Ferut, Medina, OH (US); Sarah Grace Leversee, Streetsboro, OH (US); Sanjay G. Mathias, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1161 days.

(21) Appl. No.: 13/481,323

(22) Filed: May 25, 2012

(65) Prior Publication Data

US 2013/0317346 A1 Nov. 28, 2013

(51) Int. Cl.
*A61B 5/00* (2006.01)
*A61B 5/055* (2006.01)
*G01R 33/34* (2006.01)

(52) U.S. Cl.
CPC ...... *A61B 5/0555* (2013.01); *G01R 33/34046* (2013.01); *G01R 33/34084* (2013.01)

(58) Field of Classification Search
USPC .................................................. 600/410–422
See application file for complete search history.

(56) References Cited

U.S. PATENT DOCUMENTS 5,370,118 A * 12/1994 Vij .................. G01R 33/34084
324/311
6,701,553 B1 * 3/2004 Hand ..................... A61G 7/008
5/428

(Continued)

FOREIGN PATENT DOCUMENTS

| JP | 2001-185255 A | 7/1989 |
| JP | 2010-051583 A | 3/2010 |
| WO | 2011/087495 A1 | 7/2011 |

OTHER PUBLICATIONS

JP OA for Application No. 2013-109450 Office Action dated Mar. 28, 2017.

*Primary Examiner* — Tse Chen
*Assistant Examiner* — Joanne Hoffman
(74) *Attorney, Agent, or Firm* — Dean D. Small; The Small Patent Law Group, LLC

(57) ABSTRACT

A system for magnetic resonance imaging of anatomy including a head is provided. The system includes a base member, a plurality of support members, and a plurality of articulable reception units. The plurality of support members are movably fixed to the base member and configured to translate across a surface of the base member. Each support member is releasably securable to the base member in a plurality of positions along the surface of the base member. The articulable reception units are movable from an open position to a plurality of closed positions. Each reception unit comprises at least one radio frequency (RF) receive coil disposed within a body, with the body configured for abutment with a portion of a head. Each of the plurality of articulable reception units is releasably secured in the plurality of closed positions by at least one of the plurality of support members.

20 Claims, 7 Drawing Sheets

(56) References Cited

U.S. PATENT DOCUMENTS

| | | |
|---|---|---|
| 6,762,606 B2 | 7/2004 | Jevlic et al. |
| 7,619,413 B2 | 11/2009 | Wiggins et al. |
| 8,179,136 B2 | 5/2012 | Chan et al. |
| 2004/0100346 A1 | 5/2004 | Jevtic et al. |
| 2005/0107686 A1* | 5/2005 | Chan .................. G01R 33/3415 600/422 |
| 2007/0191706 A1* | 8/2007 | Calderon ............. A61G 13/121 600/415 |
| 2008/0007259 A1* | 1/2008 | Driemel ............. G01R 33/3415 324/260 |
| 2009/0306495 A1* | 12/2009 | Scarth .................. G01R 33/307 600/415 |
| 2009/0326555 A1* | 12/2009 | Vohra ..................... A61B 19/26 606/130 |
| 2013/0076358 A1 | 3/2013 | Taracila et al. |

\* cited by examiner

ADJUSTABLE HEAD COIL SYSTEMS AND METHODS FOR MAGNETIC RESONANCE IMAGING

BACKGROUND OF THE INVENTION

The subject matter disclosed herein relates generally to magnetic resonance imaging (MRI) systems, and more particularly to systems and methods for adjustable head coils for use in conjunction with MRI systems.

MRI systems generally include a magnet to create a main magnetic field with gradient magnets exciting magnetic moments within the main magnetic field to acquire MRI data. Further, such systems also typically include a number of radio-frequency (RF) coils for receiving the MRI data that is provided to a processing unit for forming an image.

MRI images typically take a fairly long time to acquire, for example, between 15 and 45 minutes or more. During the acquisition time, the part of the body being imaged must remain generally still. For example, in order to acquire an MRI image of a patient's head, the patient is typically placed on a table with the head of the patient enclosed within one or more receive RF coil units for receiving information, such as by detecting an NMR signal. Because the size of adult heads are fairly uniform, these units typically are available in a one-size-fits-all unit, or with relatively small amounts of possible adjustment.

Children, however, experience a relatively large change in the size of their heads from birth until approximately the age of eight years old. For such children, the positioning of coils in an adult unit places the receive RF coils more than a desirable distance from their heads, resulting in reduced image quality. Further still, the distance between the child's head and head coil unit allows movement of the head during the scan, which can reduce image quality and/or require additional scans to be taken.

Some known systems attempt to address movement of heads during MRI scanning. For example, a number of pillows or cushions or other positioners may be placed in the unit interposed between the receive RE coils and the patient's head in an effort to stabilize the patient's head. Such systems, however, can be uncomfortable because the cushions are improperly sized and overly restrictive and uncomfortable. Also the use of pillows or cushions does not provide for easily controllable adjustability and/or a wide range of adjustability. Moreover, the receive RF coils remain placed an undesirably large distance from the patient's head resulting in reduced image quality. Further still, the use of such pillows or cushions packed into an adult sized unit surrounding a child's head can easily result in discomfort as well as feelings of claustrophobia or other unease.

Moreover, children especially can have significant difficulty remaining still for the required amount of time, especially in light of the feelings of claustrophobia or other unease. Accordingly, anesthesia may be used to render the child unconscious during a procedure, to prevent movement of the head. Anesthesia, however, is an expensive measure, and not without health risk to the child. Elimination of the use of anesthesia would result in a safer and less expensive scanning procedure.

BRIEF DESCRIPTION OF THE INVENTION

In accordance with various embodiments, a system for magnetic resonance imaging of anatomy including a head is provided. The system includes a base member, a plurality of support members, and a plurality of articulable reception units. The base member is removably mountable to an MRI table and is configured to support at least one of an upper body and head. The plurality of support members are movably fixed to the base member and configured to translate across a surface of the base member. Each support member is releasably securable to the base member in a plurality of positions along the surface of the base member. The articulable reception units are movable from an open position to a plurality of closed positions. The open position corresponds to a position wherein a head may be inserted or removed between the reception units. The plurality of closed positions correspond to a respective plurality of positions where the articulable reception units are proximate to a corresponding respective plurality of differently sized heads. Each reception unit comprises at least one radio frequency (RF) receive coil disposed within a body, with the body configured for abutment with a portion of a head. Each of the plurality of articulable reception units is releasably secured in the plurality of closed positions by at least one of the plurality of support members.

In accordance with other embodiments, a system for magnetic resonance imaging of anatomy including a head is provided. The system includes a base member, a first side track, a second side track, a first side support, a second side support, a first side reception unit, and a second side reception unit. The base member is removably mountable to an MRI table and comprises a generally planar upper surface. The base member is configured to support at least one of an upper body and head. The first and second side tracks extend generally laterally and are positioned proximate to the upper surface of the base member. The first side support member is movably fixed to the base member and releasably securable to the base member along a length of the first side track. The first side support member is configured to translate across the upper surface of the base member along a portion of the first side track. The second side support member is laterally opposed to the first side support member, and is movably fixed to the base member and releasably securable to the base member along a length of the second side track. The second side support member is configured to translate across the upper surface of the base member along a portion of the second side track. The first and second side reception units are each movable from an open position to a plurality of closed positions. The first and second side unite each comprise a plurality of radio frequency (RF) receive coils disposed within a body, and each are configured for abutment with a side portion of a human head. The first side reception unit is releasably secured in the plurality of closed positions by the first side support member, and the second side reception unit is releasably secured in the plurality of closed positions by the second side support member.

In accordance with yet other embodiments, a method for magnetic resonance imaging a portion of anatomy including a head is provided. The method includes providing a plurality of articulable reception units. The articulable reception units are in an open position when spaced apart to accept a human head within a volume defined by the articulable reception units. Each of the plurality of articulable reception units includes at least one radio frequency (RF) coil. The method also includes configuring the plurality of articulable reception units to allow positioning a head of a patient in a desired position for performing an MRI scan and to allow moving the plurality of articulable reception units from the open position to a closed position, wherein the plurality of articulable reception units each abut a portion of the head of the patient. The method further includes providing a plurality of support members proximate to the plurality of articulable reception units and configuring the plurality of support members to translate across a surface of a base member to which the plurality of support members are movably mounted, wherein each of the plurality of support members supports at least one of the plurality of articulable reception units in the closed position, and further configuring the plurality of support members to allow securing the plurality of support members in place to the base member.

DETAILED DESCRIPTION OF THE INVENTION

Figure 1:
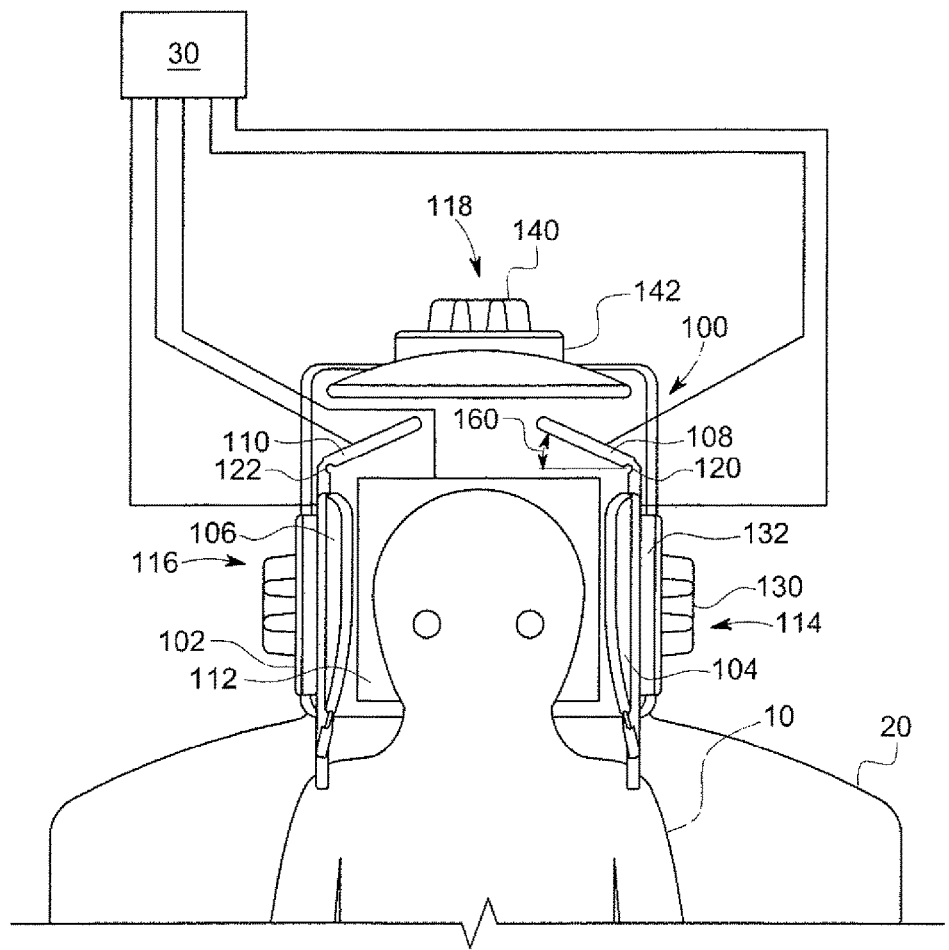
FIG. 1 is a plan view of a head coil system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "image" or similar terminology is not intended to exclude embodiments in which data representing an image is generated, but a viewable image is not. Therefore, as used herein the term "image" broadly refers to both viewable images and data representing a viewable image. However, certain embodiments generate, or are configured to generate, at least one viewable image.

Various embodiments provide systems and methods for adjustably positioning RF receive coils around a patient's head for performing a Magnetic Resonance Imaging (MRI) scan, for example to accommodate a wide variety of head sizes of child patients. In various embodiments, the imaging is implemented by providing an adjustable unit that incorporates receive coils into a padded or otherwise conformable body configured to abut a portion of a patient's head. After a patient is placed on a table configured to be inserted into an MRI bore, the unit may be adjusted to substantially conform to the patient's head, thereby securing the patient's head in a desirable position while at the same time bringing the coils into a desirably proximate location to the patient's head. Further still, the location and configuration of the coils can also reduce the amount of time required for the MRI scan.

A technical effect of at least some embodiments is improving image quality for MRI scans of variously sized heads, while also improving the stability, security, and comfort of positioning of the patient's head during the MRI scan, and/or removing the need for anesthetizing the patient. A further technical effect of at least some embodiments is reducing the amount of time required for an MRI scan. At least some embodiments provide for reduced costs and increase convenience while still providing an individually tailored fit for a wide variety of patient head sizes.

FIG. 1 illustrates a head coil system 100 formed in accordance with one embodiment. The head coil system 100 is adapted, for example, to detect NMR signals used to form an image of an anatomy of a patient 10 positioned on an MRI table 20. In the illustrated embodiment, the head coil system 100 detects NMR signals and provides corresponding information to a processing system 30 for forming an MRI image of the patient's anatomy. In FIG. 1, the head coil system 100 is shown in a first, open position with the receiving units positioned away from a patient's head to allow for easy insertion/initial placement and positioning. Once the patient is in the desired position, the head coil system 100 may be brought to a second, closed position to bring the receiving units proximate to the patient's head. With the receiving units secured in the closed position, the patient's head is stabilized to help prevent movement during the scan, and the coils are brought into a position proximate the head for improved image quality. In FIG. 1, a number of receiving units may be continuously adjusted along a given direction or directions, thereby providing for near-infinite adjustability and providing a custom fit for nearly any size head. In certain embodiments, all of the articulable receiving units may be operably linked and movable by a single actuating device. In other embodiments, only some of the receiving units may be so linked, and in still other embodiments none of the receiving units are so linked. In FIG. 1, certain of the articulable receiving units are separately moved and secured to provide greater adjustment.

The head coil system 100 includes a base 102 (also referred to as a base unit), a first side receiving unit body 104, a second side receiving unit body 106, a first crown receiving unit body 108, a second crown receiving unit body 110, and a posterior receiving unit body 112. The head coil system 100 also includes a first side support 114, a second side support 116, and a crown support 118. The receiving units generally comprise one or more receive RF coils, and are operably coupled to the processing system 30 to provide data to the processing system 30 for use in forming an MRI image of anatomy of interest, for example, the patient's head, such as the brain. The receiving unit bodies are configured to abut a portion of a patient's head. For example, the receiving unit bodies may be comprised of a molded and/or pliable (such as, for example, padded, sponge-like, or foam-like) composition to conform to the side of a patient's head. As one example, a memory foam may be used to form a portion of a receiving unit.

Embedded or otherwise disposed within the molded and/or pliable or otherwise conformable body of the receiving units are a number of RF coils configured for reception of NMR signals available from the MRI process used to form an image. Generally, the supports are coupled with the base 102 and help support and secure the receiving units in place. One or more of the supports is articulable with respect to the base 102 such that one or more of the receiving units is adjustable and may be positioned differently for different patients. Further, receiving units in different embodiments may be adjustable independently, concurrently, simultaneously, or a combination thereof. For example, in the illustrated embodiment, the first and second side receiving unit bodies 104, 106 are independently laterally adjustable with respect to a patient's head; the posterior receiving unit body 112 is fixed in position; and the first and second crown receiving unit bodies 108, 110 are adjusted and secured simultaneously longitudinally with respect to the MRI table 20 by the crown support 118, but are adjusted independently of each other laterally, respectively, by the first and second side supports 114, 116. Also, in different embodiments, the various receiving unit bodies may be physically connected, such as a by a pivot or joint; physically separate; integrally formed as part of a single unit; and/or a combination thereof.

The base 102 is generally sized, shaped, and configured to support a portion of the patient's upper body, including the head of the patient, during an MRI scan. The base 102 is removably coupled with the MRI table 20, so that different supports or bases may be used in different procedures. Thus, an MRI table used with the head coil system 100 may be interchangeably used with other coil arrangement systems, and thus may be used with different MRI systems. For example, an MRI system including a bore, table, and associated processing unit may be provided with a standard adult head coil unit as well as an adjustable unit (instead of multiple sized units) as described herein for use with children.

The first side receiving unit body 104 is generally positioned so that coils disposed within the first side receiving unit body 104 are oriented laterally inward toward a side of a patient's head (lateral being understood as corresponding to the width of the MRI table 20 and/or base 102, and longitudinal being understood as corresponding to the length of the MRI table 20 and/or base 102). The first side receiving unit body 104 is configured to abut a side of the patient's head. As discussed above, the first side receiving unit body 104 is generally pre-formed and/or pliable to conform to the side of the patient's head. For example, the first side receiving unit body 104 in the illustrated embodiment comprises a pre-formed pad disposed within a thin flexible shell. The pad is pre-formed to generally match the shape of the side of a human head, but is also made of a pliable material so that the pad may be shaped even more closely to an individual head when brought against the side of the individual head. In other embodiments, receiving units may be made, for example, of molded or otherwise pre-shaped construction; a plate supporting a flexible, pliable material; or a generally uniform pliable construction, such as a foam- or sponge-like; or may be a memory foam.

The first side receiving unit body 104 has a plurality of RF receive coils embedded or encased within its padding. This placement of coils within a body, for example, a pliable unit of padding, allows for improved positioning of the coils proximate to the head (for example, when compared to units where the coils remain stationary and pillows or other cushioning is placed between the coils and a patient's head). This also allows for a cleaner, more streamlined appearance of the unit, and helps alleviate feelings of claustrophobia or other discomfort that may make it difficult for patients, especially younger patients, to remain still during an MRI procedure.

The first side receiving unit body 104 is operably connected with the first side support 114 to allow generally lateral adjustment (relative to the MRI table 20 and/or the head of a patient) of the first side receiving unit body 104, thereby accommodating a variety of widths of heads. In FIG. 1, the head coil system 100 is shown in an open position with the side and crown receiving units, including first side receiving unit body 104, positioned away from the patient's head. Because the first side receiving unit body 104 is conformable to the side of a patient's head, the first side receiving unit body 104 can be positioned with the coils of the first side receiving unit body 104 quite close to the patient's head.

The coils disposed within the first receiving unit body 104 may be flexible or otherwise. For example, the coils may be generally rigid, but positioned with enough padding between the coils and the patient's head so that the padding may conform to a patient's head without requiring flexibility of the coils. As another example, the coils may be preconfigured in a molded receiving unit that is generally formed to align or correspond with the side of a patient's head. In still other embodiments, the receiving unit may be discontinuously conformable, that is, have bendable or otherwise jointed segments or portions that articulate with respect to each other, with coils located in respective segments or portions. As another example, the coils themselves may also be flexible, and positioned within a pliable structure, such as padding, such that substantially all of the receiving unit is continuously pliable or conformable. As an example, the coils may comprise Kapton. In other embodiments, the coils could be formed of a copper material and supported by plastic. The coils are sized and configured for imaging the patient's head. For example, in certain embodiments, the first side receiving unit body 104 may comprises a total of 8 loop coils, and the head coil system 100 comprises a total of 32 coils. The second side receiving unit body 106 is generally similar to first side receiving unit body 104, and is positioned laterally opposed to the first side receiving unit body 104.

The first side support 114 includes a first articulation member, for example, a knob 130, and first support plate 132. The knob 130 is associated with a threaded rod or other gear-type mechanism (not shown) such that when the knob 130 is turned in a first direction, the first side support 114 is urged inwardly toward a patient's head, and when turned in a second, opposite direction, the first side support 114 is urged outwardly away from a patient's head. Thus, in the illustrated embodiment, the first side support 114 translates across a surface of the base 102 and is adjustable in a generally continuous fashion. Alternatively or additionally, the first side support 114 (and/or other supports discussed herein) may also be rotatably mounted, for example by a hinge, to the base 102, to provide additional versatility in the positioning of the supports. In still other embodiments, the first side support 114 (and/or other supports discussed herein) may include a hinge pivotably connecting, for example, upper and lower portions of the first side support 114. For example, during an emergency situation, a practitioner may quickly pivot a hinged support to obtain quick access to a patient's head. In other embodiments, the first side support 114 is adjustable in a series of discrete steps. For example, the first articulation member may include a member associated with and movable between a series of notches that are configured to secure the first side support 114. The first support plate 132 is configured to provide support to the first side receiving unit body 104, and to help secure the first side receiving unit body 104 at or near the side of a patient's head when the system 100 is in the closed position. For example, the first side support 114 may be releasably secured in place by friction within the knob mechanism and/or a separate locking mechanism (not shown), such as a thumbscrew, or, as another example, via a ratcheting mechanism. The first side support 114 may be released from its secured position by turning the knob and/or unlocking the locking mechanism.

In the illustrated embodiment, the first side receiving unit body 104 is joined to the first side support 114. For example, the first side receiving unit body 104 may be adhesively joined to the first support plate 132. In other embodiments, receiving units may be held to supports by one or more fasteners or other joining technology. In still other embodiments, all or a part of the support may be integrally formed with at least a portion of a receiving unit. In yet still other embodiments, the side supports and side receiving units may not be joined, and may interact only when the side support is urged against the side receiving unit. In such embodiments where the support and receiving unit are joined, the support may act not only to support, but also to articulate the receiving unit either toward or away from a patient's head. In embodiments where the support and receiving unit are not joined, the receiving unit may be initially positioned by hand, with the support then brought inwardly to secure the receiving unit in the position at which the receiving unit has been manually placed. In still other embodiments, the receiving unit and support may not be joined, but the support may still be used to articulate the receiving unit inwardly, for example, via a sliding contact between the support and the receiving unit, and/or the receiving unit may resiliently move away from a patient's head when the support unit is withdrawn.

In the illustrated embodiment, the side support and receiving unit are adjustable in a substantially straight line. In other embodiments, the support and/or receiving unit may also be adjustable by swiveling or otherwise pivoting about a vertical axis or plane (with vertical understood as being oriented generally perpendicular to the plane of the MRI table 20) and/or tilting or otherwise pivoting about a horizontal plane or axis (with horizontal being oriented generally parallel to the plane of the MRI table 20). Thus, the supports and/or receiving units may be articulable in a generally linear fashion with additional adjustments also possible. The second side support 116 is generally similar to the first side support 114, and is positioned laterally opposed to the first side support 114.

In the illustrated embodiment, the first side receiving unit body 104 is mechanically joined to first crown receiving unit body 108. In the embodiment of FIG. 1, a joint 120 connects the first side receiving unit body 104 with the first crown receiving unit body 108. The first crown receiving unit body 108 is pivotable about the joint 120 with respect to the first side receiving unit body 104. Thus, the coil head system 100 is able to provide a degree of longitudinal adjustment for fitting a patient's head in addition to the lateral adjustment provided by the adjustability of the sider receiving units. For example, the joint 120 may be formed by a pin accepted by a hole, or other hinge-type mechanism. As another example, a portion of the first crown receiving unit body 108 may be integrally formed with a portion of the first side receiving unit body 104, with the joint 120 formed by, for example, a resiliently bendable section defining a boundary between the side and crown receiving units.

As with the side receiving units, the first crown receiving unit body 108 of the illustrated embodiment is configured to abut the patient's head, with the first crown receiving unit body 108 configured to abut a portion of the top, or crown, of a patient's head. In the illustrated embodiment, the first crown receiving unit body 108 comprises a padded structure that conforms to the shape of the portion of a patient's ahead against which it is urged. In other embodiments, the first crown receiving unit body 108 may comprise a structure that is molded or otherwise pre-formed to generally correspond to the desired portion of a patient's head additionally or alternatively to the padded structure.

Generally speaking, the construction of the first crown receiving unit body 108 is similar to that of the side receiving unit bodies. For example, the first crown receiving unit body 108 may have coils embedded or otherwise disposed within a volume that is padded and/or molded and/or otherwise configured to conform to and/or abut a portion of a patient's head. In the illustrated embodiment, the first crown receiving unit body 108 is joined to the first side receiving unit body 104. However, in other embodiments the side and crown receiving units could be separate and/or joined to other receiving units. Also, in the illustrated embodiment, a first crown receiving unit body 108 and a second crown receiving unit body 110 are shown. In other embodiments, there may only be a single crown receiving unit, more than two crown receiving units, or no crown receiving unit at all.

In certain embodiments, the coils provided within the crown receiving unit or units differs in configuration from the coils provided within one or more side receiving units. For example, the side receiving units may comprise overlapping loop coils. However, the crown receiving unit or units may comprise one or more saddle coils.

In the illustrated embodiment, the second crown receiving unit body 110 is generally similar to the first crown receiving unit body 108, but is joined to the second side receiving unit body 106 by a joint 122.

As indicated above, the first crown receiving unit body 108 is joined to the first side receiving unit body 104 via joint 120. The first crown receiving unit body 108 extends generally at an angle 160 inward laterally and upward longitudinally to extend over the upper portion of one side of a patient's head. The first crown receiving unit body 108 is movable at a pivot point of the joint 120 to change the angle 160. In other embodiments, a crown receiving unit may be articulable more generally longitudinally, or put another way, more generally perpendicular to the lateral travel of the side receiving units. In other embodiments, one or more crown receiving units may be articulated inwardly or outwardly at a generally constant angle to the longitudinal and lateral directions, that is, along a line that is neither generally parallel nor generally perpendicular to a lateral line defined by the side receiving units. In addition to movement along such a line, crown receiving units may also be configured to allow for swiveling and/or tilting as discussed above with respect to the side receiving units.

Unlike the first side receiving unit body 104, the first crown receiving unit body 108 is not support or articulated by the first side support 114. Instead, the first crown receiving unit body 108 is supported by the crown support 118. The crown support 118 also supports the second crown receiving unit body 110. The crown support 118 may be similar in many respects to the above discussed side supports in terms of structure and movability. For example, the crown support 118 includes a knob 140 and a support plate 142 similar to those discussed above for the side supports. However, in the illustrated embodiment, the crown support 118 is not joined to either of the crown receiving units. Instead, the crown support 118 urges the crown receiving units inwardly as the crown support 118 is urged inwardly and into contact with the crown receiving units (or, as depicted in FIG. 1, downward in a longitudinal direction). Thus, the crown support 118 may be articulated to bring the crown receiving units into a closed position.

The closed position in some embodiments is with both crown receiving units pressed against an upper portion of the patient's head. In other embodiments, the crown supports may be merely brought closely to the upper portions of a patient's head. In the illustrated embodiment, the crown support 118 is adjustable generally continuously along a line of action, providing a wide range of fine-tuning for a plurality of closed positions each custom tailored to an individual patient's head. Similar to the side supports, in other embodiments, the crown support may also be adjustable to pivot about such a line of action and/or tilt with respect to the MRI table 20 and/or base 102, and/or have a series of notches or other pre-configured discreet points for setting a closed position.

The head coil system 100 also includes a posterior receiving unit body 112. In the illustrated embodiment, the posterior receiving unit body 112 is not generally articulable, but is instead mounted directly to the base 102. The posterior receiving unit body 112, similar to the other receiving units, includes an arrangement of coils embedded or otherwise disposed within a body configured for contact with a portion of the patient's head. The posterior receiving unit body 112 is configured for contact with the back, or posterior of a patient's head, and may also include an extension for contact with, for example, the neck and/or shoulders of a patient for additional support and positional security. The posterior receiving unit body 112 may also be padded or cushioned to conform to a patient's head when contacted, and/or may include a molded or otherwise pre-formed surface configured to accept the back of a patient's head. Similar to the side receiving units, the posterior receiving unit body 112 may have loop coils arranged therein, for example, an arrangement of overlapping loop coils.

A combination of lateral and/or longitudinal and/or other adjustments as discussed above provides a wide range of adjustment to fit a wide variety of head sizes, accommodating variation in both length and width. A system, such as the head coil system 100, may reduce the feeling of claustrophobia or other discomfort, and may provide a more comfortable secure fit to provide for increased patience convenience and reduced risk of requiring additional scanning due to movement. With the supporting units mounted to the base and supporting the receiving units, the head coil system 100 also may provide for improved stability instead of using cushions inserted into a head coil, or as another example, instead of a wearable coil configuration for other parts of the anatomy. Further, the head coil system 100 also may provide for improved positioning of RF receive coils nearer to each individual patient's head and thereby improve image quality.

Further still, with receiving units having a range and type of adjustment as discussed in connection with the illustrated embodiments, embodiments may provide improvements for use with, for example, surgical MRI techniques. For example, in certain procedures, it is desirable to perform a surgical technique or techniques between MRI scans, for example, to identify a level of change obtained by the surgical technique or techniques. A system formed in accordance with certain embodiments, such as head coil system 100, may provide for greater ease in attaching or detaching the head coil system during such procedures. For example, after an initial scan, the side and/or crown supports and receiving units may be moved outwardly (from the closed to an open position) to allow for access for a surgical technique or techniques. Then, after the technique or techniques are performed, the receiving units and supports may be returned from the open position to their previous closed position, and another scan performed. Further still, markings may be provided on the supports and/or base to allow a practitioner to identify the position of the receiving units during the initial scan and match that position for the second scan for consistency of positioning and imaging.

The above described embodiment includes a separate non-movable posterior receiving unit along with separate, independently movable side receiving units connected to respective crown receiving units. Other configurations are also contemplated in different embodiments. For example, the system 200 depicted in FIG. 2 includes an articulable crown receiving unit and articulable side receiving units that are contiguous with a non-articulable posterior receiving unit. The posterior, sides, and crown are formed as an integral unit 220, with the sides and crown configured as foldable, bendable, or otherwise biasable wing like structures that are pivotable with respect to the posterior receiving unit. The pivoting motion may include a continuous pivoting effect provided by a resiliently biasable receiving unit that is bendable or pliable along the length of the receiving unit. In other embodiments, the pivoting motion may be restricted to a single point of bending, or, in still other embodiments, may be accomplished by a bending or pivoting action at a series of points disposed along a length of a receiving unit.

Such receiving units may be formed as a generally unitary structure, with a single shell or other structure comprising biasable portions and appropriately located and configured coils within the various portions of the shell or other structure. Such a structure, for example may be a shell surrounding a padding material with coil arrays embedded therein at different locations corresponding to different portions of a head, or may comprise a foam-like, sponge-like, or otherwise pliable structure with coils embedded within. In still other embodiments, generally rigid individual portions or segments may be provided that are articulable with respect to each other. In still other embodiments, portions or receiving units may be separately formed from other portions and receiving units, and joined by, for example a pivot or hinge.

Figure 2:
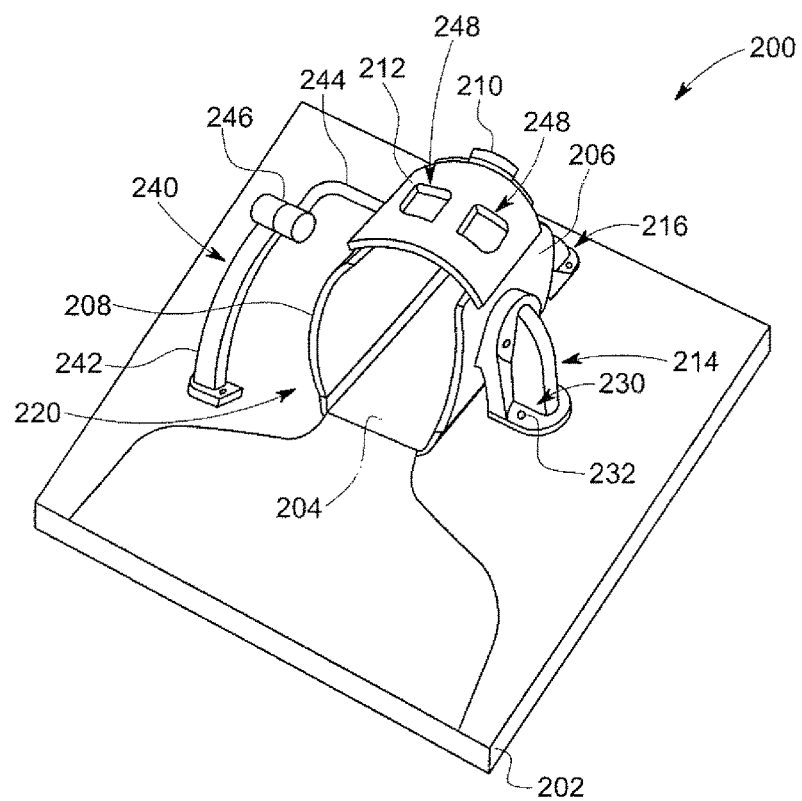
FIG. 2 is a perspective view of a head coil system in accordance with various embodiments.

FIG. 2 illustrates an embodiment of a head coil system 200 for adjustable positioning and securing of a variety of differently sized heads for MRI scanning. The head coil system 200 includes a base 202, a posterior receiving unit 204, a first side receiving unit 206, a second side receiving unit 208, a crown receiving unit 210, and a front receiving unit 212. Further, the head coil system includes a first support 214 (associated with the first side receiving unit 206), a crown support 216 (associated with the crown receiving unit 210), and a third support (not shown, associated with the second side receiving unit 208). The head coil system 200 also includes an anterior, or front receiving unit 212 and associated front (anterior) support 240. The front receiving unit 212 also includes embedded coils, and allows for the placement of coils around substantially the circumference of a patient's head, in contrast with the head coil system 100, which is generally open with the respect to the face, or front or anterior portion of a patient's head. Such an arrangement substantially surrounding the circumference of a head and/or providing coils corresponding to and located proximately to the front of a head may provide for improved imaging, but also in a less open design that may, in some instances, reduce overall patient comfort.

The base 202 is configured similarly in certain respects to the previously discussed base 102. The base 202 is generally sized, shaped, and configured to support a portion of the patient's upper body, including the head of the patient, during an MRI scan. The base 202 is removably coupled with an MRI table, so that different supports or bases may be used in different procedures. Thus, the head coil system 200 may be interchangeably used with other systems for use with a standard MRI system, therefore reducing costs and not requiring multiple MRI systems to be purchased or purpose-built for use with different procedures and patients. The base 202 is generally sized, shaped, and configured to support a portion of the patient's upper body, including the head of the patient, during an MRI scan.

As also discussed above, the posterior receiving unit 204, first side receiving unit 206, second side receiving unit 208, and crown receiving unit 210 are formed integrally as part of the integral unit 220, with the posterior receiving unit 204 secured to the base 202 and the first side receiving unit 206, second side receiving unit 208, and crown receiving unit 210 configured to be bendable or otherwise articulable with respect to the mounted posterior receiving unit 204. In the illustrated embodiment, the first side receiving unit 206, second side receiving unit 208, and crown receiving unit 210 are free to bend upwardly away from the base 202 and inwardly toward a portion of the patient's head. For example, a given receiving unit may be articulated in a generally continuous bend of pliable material forming a portion of the integral unit 220 as depicted in FIG. 2. As another example, a given receiving unit may articulate at a joint or joints formed by bendable portions generally defining a boundary between the posterior receiving unit 204 and the given receiving unit being articulated with respect to the posterior receiving unit 204.

Each of the given receiving units in such embodiments may also be considered to be a portion or sub-portion of the integral unit 220, with each particular position or sub-portion generally defined by the shape of that particular position or sub-portion (generally configured to be positioned proximate to a given portion of a patient's head with the system 200 in the closed position) as well as the arrangement of coils located within the sub-portion (for example, the crown and side portions may have differing coil arrangements, as also discussed above). Once a given receiving unit is positioned as desired, for example by hand positioning by a practitioner preparing the patient for the MRI scan, the appropriate corresponding support may be positioned to secure the receiving unit in place.

The first support 214, crown support 216, and third support are generally similar in many respects for the depicted head coil system 200, so only a discussion of one will be provided. Different types of supports (for example, support structures using a knob mechanism as discussed above, or, as another example, using a rack-and-pinion mechanism to articulate supports) may be used in different embodiments. Different types of supports may be used within the same embodiment as well. Further, in some embodiments, more than one support and/or type of support may be used for a given receiving unit.

The first support 214 includes a hole 230 that accepts a fastener 232. A corresponding slot or track (not shown) in the base 202 also accepts the fastener 232. The first support 214 may be advanced generally along the line of the slot or track until the first support 214 is in a desired position, at which point the fastener (for example a bolt including a threaded member accepted by a nut and washer combination positioned underneath the slot or track) is tightened to secure the support (and corresponding receiving unit supported by the support) in place in the desired position. The length and positioning of the slot or track is chosen to provide for a range of motion to accommodate variously sized patient heads. To release the support (and corresponding unit) the fastener 232 is loosened to allow withdrawal of the support and receiving unit.

In other embodiments, a hole may be provided in the base and a corresponding slot provided in the first support. In still other embodiments, both may be slotted. In still other embodiments, a tab or other projection may be accepted by a slot or track alternatively or additionally to a fastener. In yet still other embodiments, a slot or track and corresponding hole and fastener and/or tab is positioned on both sides of the support. Additionally, an appropriate clearance may be selected between the slot or track and fastener or tab to allow for swiveling or pivoting thus allowing the support to be oriented at an angle to the slots or tracks. Further still, a shim, tapered device, or other mechanism may be used to allow the support to be tilted or angled upwardly or downwardly with respect to the base 202.

The front receiving unit 212 is configured to be oriented toward the front of a patient's head when the system 200 is in a closed position, and provides for the positioning of coils oriented toward the front of a patient's head. When used in conjunction with the coils of side and posterior receiving units, this provides for an arrangement of coils substantially surrounding a circumference of a patient's head. The front receiving unit 212 in the illustrated embodiment is configured as an eyepiece, or mask, that pivots up and away from the patient's face to an open position. The front support 240 includes a first arm 242 and a second arm 244 joined by a pivoted joint 246. The pivoted joint 246 may be, for example, a hinge or pin. The first arm 242 is mounted to the base 202 extends generally upward with respect to a plane defined by the base 202. The second arm 244 is joined to the front receiving unit 212. By moving the second arm 244 about the pivoted joint 246, the front receiving unit 212 may be moved between a first, or open, position away from the front of a patient's head, and a second, closed position proximate to the front of a patient's head. The pivoted joint 246 may be configured so that the front receiving unit 212 is lockable in the open and/or closed positions.

To provide for a more open configuration when desired, the eyepiece, or front receiving unit 212 may be left in the up, or open position, when the remaining receiving units are in the closed positions. In the illustrated embodiment, the front receiving unit 212 in the closed position rests against the side receiving units 206, 208, thereby providing for some space, or breathing room, between the front receiving unit 212 and the patient's face, helping to increase patient comfort and reducing sensations of claustrophobia or other discomfort. In other embodiments, the front receiving unit 212 may be brought into contact with a patient's face. In such embodiments, the front receiving unit may, for example, be molded or otherwise pre-shaped and/or be comprised of a padded or otherwise pliable construction so that the front receiving unit conforms to the contours of the portion of the patient's head with which the front receiving unit comes into contact.

The front receiving unit 212 includes eye openings 248. The eye openings 248 allow patients to see their surroundings even in the closed position, which may further reduce any feelings of claustrophobia or other unease. Further still, the front receiving unit 212 may be shaped and configured with a design to help put younger patients at ease, such as appearing to be part of a superhero's costume and/or to match a theme depicted inside the bore of the associated MRI system to provide entertainment and/or a distraction or diversion to make the scanning experience more pleasant for younger patients.

Figure 3:
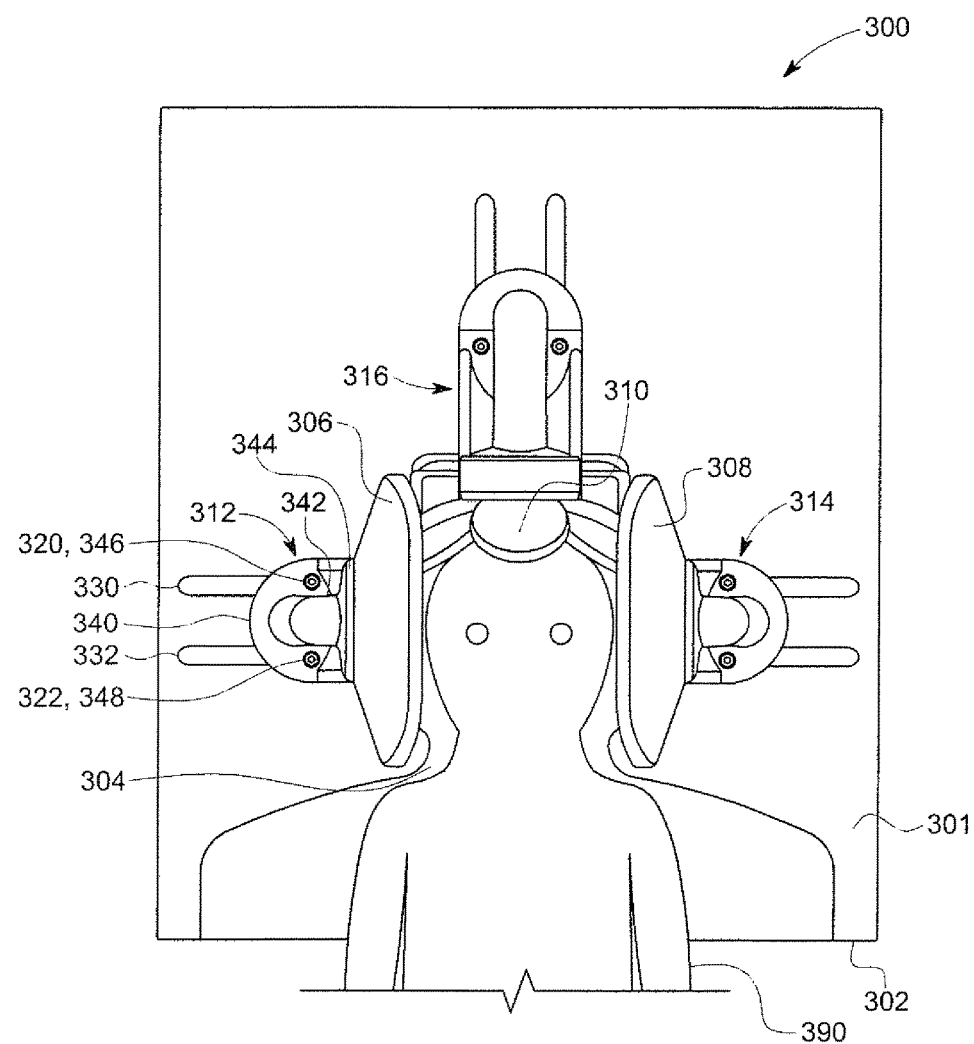
FIG. 3 is a plan view of a head coil system in accordance with various embodiments.
Figure 4:
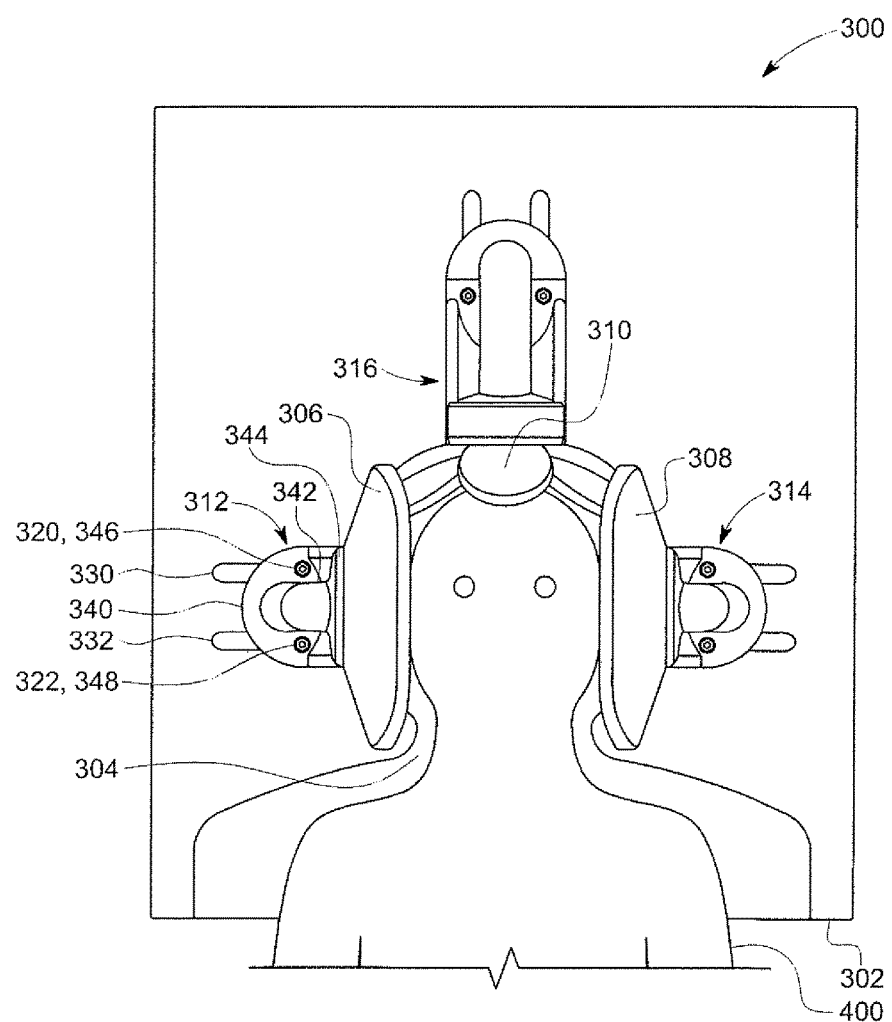
FIG. 4 is another plan view of the head coil system of FIG. 3 with a larger patient in place.

FIG. 3 illustrates a head coil system 300 in a closed position over a first smaller patient 390 and FIG. 4 shows the head coil system 300 over a second larger patient 400. For example, the patient 390 in FIG. 3 may be about two months old, and the patient 400 in FIG. 4 may be about 5 years old. As seen in the depicted embodiment, the head coil system 300 is configured with a sufficient range of movement (for example, by appropriately sizing and configuring slots or tracks associated with the movable supports) to provide a wide variety of potential closed positions to accommodate a wide variety of head sizes, and with generally continuous adjustment between the positions. For example, the head coil system 300 may be configured to provide a range of adjustment to accommodate patient head sizes corresponding to patients ranging in age from birth to about eight years old. In other embodiments, even greater ranges may be provided. For example, in a head coil system configured to work with children and/or adult patients, a range of adjustment between a closed position and open position may be selected to provide adequate clearance for access to perform a surgical technique or techniques between scans, as also discussed above. The head coil system 300 depicted in FIGS. 3 and 4 includes independently adjustable side receiving units and an independently adjustable crown receiving unit.

The head coil system 300 includes a base 302, a posterior receiving unit 304, a right receiving unit 306, a left receiving unit 308, and a crown receiving unit 310. The head coil system 300 also includes a first support 312 (corresponding to the right receiving unit 306), a second support 314 (corresponding to the left receiving unit 308), and a third support 316 (corresponding to the crown receiving unit 310).

The base 302 is similar in many respects to the previously discussed bases 102, 202. The base 302 is generally sized, shaped, and configured to support a portion of the patient's upper body, including the head of the patient, during an MRI scan. The base 302 is removably coupled with an MRI table, so that different supports or bases may be used in different procedures. Thus, the head coil system 300 may be interchangeably used with other systems for use with a standard MRI system. The base 302 is generally sized, shaped, and configured to support a portion of the patient's upper body, including the head of the patient, during an MRI scan.

In the embodiment illustrated in FIGS. 3 and 4, the crown receiving unit 310 is first urged into contact with the crown of the patient's head, and the receiving units 306, 308 are then urged into contact with the sides of the crown receiving unit 310 and/or the sides of the patient's head, depending on the size of the patient's head and the width of the crown receiving unit 310. In other embodiments, the side receiving units may initially be urged into contact with the sides of the patient's head, with the crown receiving unit subsequently urged downwardly (or toward the patient) into position after the side receiving units are positioned as desired. In such embodiments, the side receiving units and their corresponding supports may provide additional support to the crown receiving unit, and/or the crown receiving unit and its corresponding support may provide additional support to the side receiving units.

In the embodiment depicted in FIGS. 3 and 4, the crown and side receiving units are advanced along lines generally perpendicular to each other, with the crown receiving unit advanced generally longitudinally with respect to the base 302 and/or MRI table associated with the head coils system 300, and the side receiving units advanced generally laterally with respect to the base 302 and/or MRI table. In other embodiments, differently sized, configured, and/or oriented receiving units may be urged into a closed position contacting and/or proximate to a patient's head from different angles or along different lines of action.

The receiving units in the illustrated embodiment have a general construction generally similar to the above discussed receiving units in many respects. For example, the receiving units of the head coil system 300 include an arrangement of coils disposed within a padded or otherwise pliable volume or body that is configured to abut the side of a patient's head during an MRI procedure. The receiving units, or portions thereof, may further be molded, bent, or otherwise preformed to generally correspond to a typical profile or shape of the portion of a human head to which they are designed to abut.

In the illustrated embodiment of FIGS. 3-4, the side and crown receiving units are joined, such as by an adhesive or fastener, to their corresponding support. The first support 312, second support 314, and third support 316 are generally similar for the depicted head coil system 300, so a discussion of only one will be provided. In other embodiments, different types of supports (for example, using a knob mechanism as discussed above, or, as another example, using a rack-and-pinion mechanism to articulate supports) may be used in different embodiments. Again, different types of supports may be used within the same embodiment as well. Further, in some embodiments, more than one support and/or type of support may be used for a given receiving unit.

The first support 312 includes a base 340 and a support plate 344 joined by an arm 342. The base 340 is configured to rest atop the base 302, as well as traverse across a generally planar surface 301 of the base 302, and the support plate 344 is configured to support a corresponding receiving unit. The first support 312 also includes first and second fasteners 320, 322 that are accepted by corresponding first and second openings 346, 348 in the base 340 of the first support 312 and corresponding first and second slots 330, 332 in the base 302. The first and second slots 330, 332 are generally parallel to each other and disposed on opposite sides of the base 340 of the first support. The first and second slots generally define both the direction and amount of travel for their corresponding support. The length and positioning of the slots is chosen to provide for a range of motion to accommodate variously sized patient heads. The first support 312 may be advanced generally along the line of the first and second slots until the first support 312 is in a desired position, at which point the first and second fasteners 320, 322 are tightened to secure the first support 312 (and corresponding receiving unit supported by the support) in place in the desired position.

The above discussed slot and fastener arrangement describes but one example of the use of a track to guide the movement of support structures. Such a track facilitates a generally linear path of travel along a surface of the base and also interconnects the movable support structure and the base, as well as facilitating the releasable securement of the support unit along a length of the track. Other track arrangements are possible, including, for example, a threaded rod, worm gear arrangement, rail, or rack of a rack-and-pinion assembly. Track structures may be mounted on one or both of a support and base. Moreover, a given support may have one track associated therewith, or a plurality of tracks associated therewith.

Other arrangements may also be provided in alternate embodiments. By way of example, in other embodiments, a hole may be provided in the base and a corresponding slot provided in a support member. In still other embodiments, both may be slotted. In still other embodiments, a tab or other projection may be accepted by a slot or track alternatively or additionally to a fastener. Additionally, an appropriate clearance may be selected between the slot and fastener or tab to allow for swiveling or pivoting to allow the support to be oriented at an angle to the slots or tracks. Further still, a shim, tapered device, or other mechanism may be used to allow a support to be tilted or angled upwardly or downwardly with respect to the base 302. The supports and corresponding openings, fasteners, and slots, provide an example of an adjustment assembly that facilitates a continuous range of adjustability throughout an adjustment range for a given support. In alternate embodiments, as also discussed above, notches or detents may be provided to provide for a plurality of pre-selected discreet positions.

As can be appreciated by a consideration of the embodiments discussed above including the depictions of FIGS. 3 and 4, a wide range of patient head sizes can be accommodated by embodiments. For example, the use of support members that are movably engaged for translation across the surface of a base member (for example, through the use of slots, knobs and threaded mechanisms, worm gears, or rack and pinion assemblies) allows for a considerably large range of motion laterally and longitudinally (or along other lines) of the support members. This range of motion in turn allows for a corresponding large range of motion for the reception units associated with the support members (by example, by being joined to and/or supported by the support members). This large range of motion allows the reception units to be secured at a plurality of wide ranging closed positions that can accommodate a corresponding wide variety of patient head sizes. For example, in embodiments, the plurality of head sizes correspond to sizes of heads corresponding to patients ranging in age from new born to eight years of age.

As discussed above, receiving units formed in accordance with certain embodiments include an arrangement of coils disposed within the volume of a receiving unit. Such a receiving unit may also be considered a positioning unit, as the receiving unit is configured to abut the side of a patient's head thereby helping to position the patient's head and/or maintain the patient's head in a desired position. Thus the receiving unit can allow not only placing coils in a desired close proximity to a patient's head, but also stabilizing the patient's head in a desired position. In certain embodiments, different coil arrangements are provided for receiving units configured to abut or be proximate to different portions of a patient's head.

Figure 5:
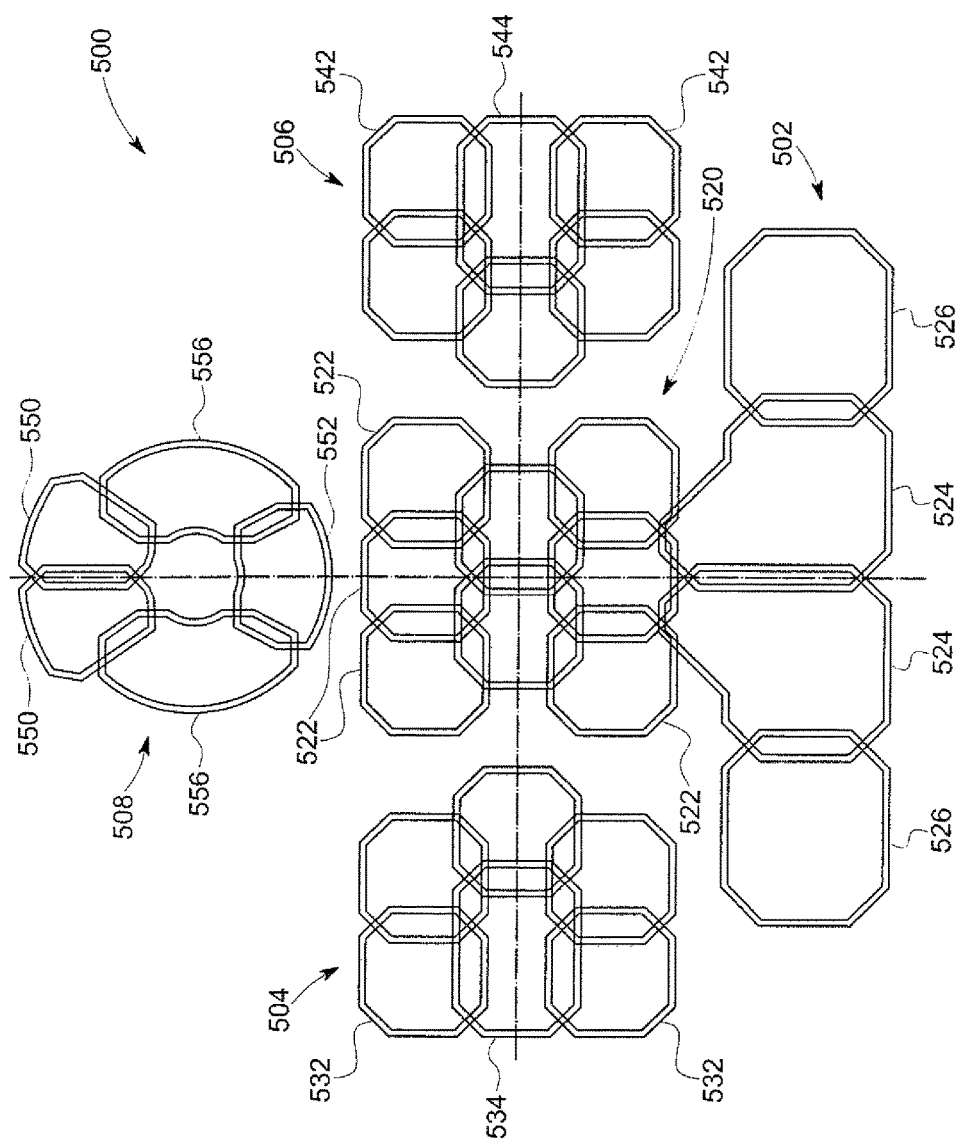
FIG. 5 is a schematic view of a coil arrangement in accordance with various embodiments.

FIG. 5 illustrates a schematic view of a coil arrangement 500 of a head coil system formed in accordance with certain embodiments. The coil arrangement 500 includes a posterior arrangement 502 (for embedment or disposition within a corresponding posterior receiving unit), a right side arrangement 504 (for embedment or disposition within a corresponding right receiving unit), a left side arrangement 506 (for embedment or disposition within a corresponding left receiving unit), and a crown arrangement 508 (for embedment or disposition within a corresponding posterior receiving unit). The arrangement depicted in FIG. 5 is schematic in nature, and does not necessarily imply any specifics regarding the receiving unit construction.

For example, an arrangement such as coil arrangement 500 may be employed in an embodiment featuring integrally formed right, posterior, left, and crown receiving units, or may also be employed in an embodiment where some or all of the receiving units are distinctly and separately formed. Further such an arrangement may be used in a system where the receiving units are bent or pivoted into place, as well as embodiments where the receiving units are slid into place, or in still further embodiments employing additional or alternative positioning movements.

The posterior arrangement 502 includes a variety of size of coils. For example, the posterior arrangement includes a first posterior array 520 that includes a plurality of similarly sized overlapping loop coils 522. The posterior arrangement also includes larger first coils 524 and second coils 526 disposed below, or inferior, to the first posterior array 520. The posterior arrangement is generally symmetric about a center line running longitudinally.

The right side arrangement 504 also includes overlapping loop coils. In the depicted coil arrangement 500, the right side arrangement includes five similarly sized coils 532 positioned generally about a larger coil 534. The left side arrangement 506 includes coils 542 and larger coil 544, and is generally symmetric to the right side arrangement 504 about a center line running longitudinally.

The crown arrangement 508 of the coil arrangement 500 differs from the arrangements for the other receiving unit coils, for example, in the shape of the coils of the crown arrangement. The crown arrangement 508 includes first coils 550, second coil 552, and third coils 556. The crown arrangement 508 is generally symmetric about a center line running longitudinally. The third coils 556, disposed generally on either side of the crown arrangement 508, are saddle-shaped and may be referred to as saddle-coils. Such an arrangement of dual saddle-coils positioned within a crown receiving unit can improve image quality.

Figure 6:
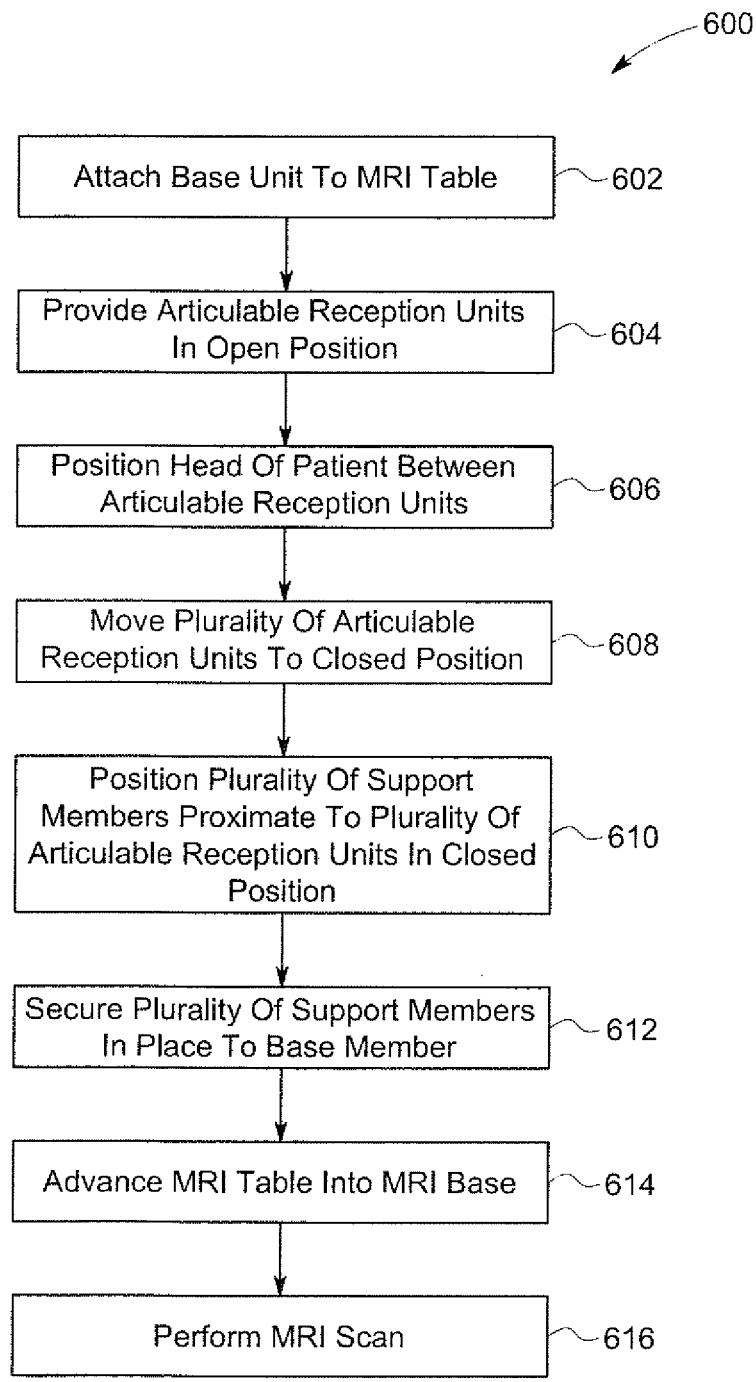
FIG. 6 is a flowchart of a method of magnetic resonance imaging in accordance with various embodiments.

FIG. 6 provides a flowchart for a method 600 of magnetic resonance imaging. In certain embodiments, certain steps may be added or omitted, certain steps may be performed simultaneously with other steps, certain steps may be performed in different order, and certain steps may be performed more than once, for example, in an iterative fashion.

The depicted method 600 begins at 602, with a base unit attached to an MRI table. The base unit, for example, may be similar to the above discussed base units 102, 202, 302. Articulable reception units associated with the base unit are positioned in an open position (at 604). Each reception unit includes RF receive coils, and is generally configured for proximate positioning to a portion of a head. The reception units, for example, may be substantially similar to certain units discussed above in connection with systems 100, 200, 300. In such an open position, the articulable reception units are spread to provide a space within which a patient's head may be positioned between the articulable reception units.

Next, at 606, the head of the patient is placed in a desired position between the articulable reception units still in the open position. At 608, the articulable reception units are moved to a closed position. In the closed position, the articulable reception units are positioned proximately and/or in abutment with the patient's head. This close positioning at or near the head of the patient allows for improved image quality, as the RF receive coils within the articulable reception units are positioned close to the anatomy being scanned. For example, the plurality of articulable reception units may include first and second side reception units. The first and second side reception units may be moved from the open to closed position by bending or pivoting the first and second side reception units. Alternatively, the first and second side reception units may be moved from the open to the closed position by sliding laterally inwardly first and second side support members that are associated with the first and second side reception units.

At 610, the plurality of support members are positioned proximate to the plurality of articulable reception units in the closed position. In this position, the support members are positioned to support and maintain the articulable reception units (and therefore the patient's head) in the desired position for scanning. The support members may be positioned, for example, by translating the support members across a surface of a base member to which they are removably attached. This may be accomplished, for example, via a slot or track arrangement as discussed above.

In certain embodiments where the support members are permanently or semi-permanently attached to the support members (by, for example, adhesive joining, use of fasteners or other devices, or by being formed integrally with at least a portion of each other), at 608 and 610 are performed simultaneously. In other embodiments, for example where there is no permanent or semi-permanent connection between a given support member and its corresponding articulable receiving unit, step 610 may or may not be performed subsequently to step 608.

Next, at 612, with the plurality of support members positioned as desired proximate to the plurality of articulable reception units, the support members are secured in place to the base member. With the support members secured in place, the associated reception units are thus also secured in place.

At 614, with the patient's head securely positioned by the previous steps, the MRI table (and therefore patient as well) is advanced into the MRI bore, where a scan is performed at 616.

Figure 7:
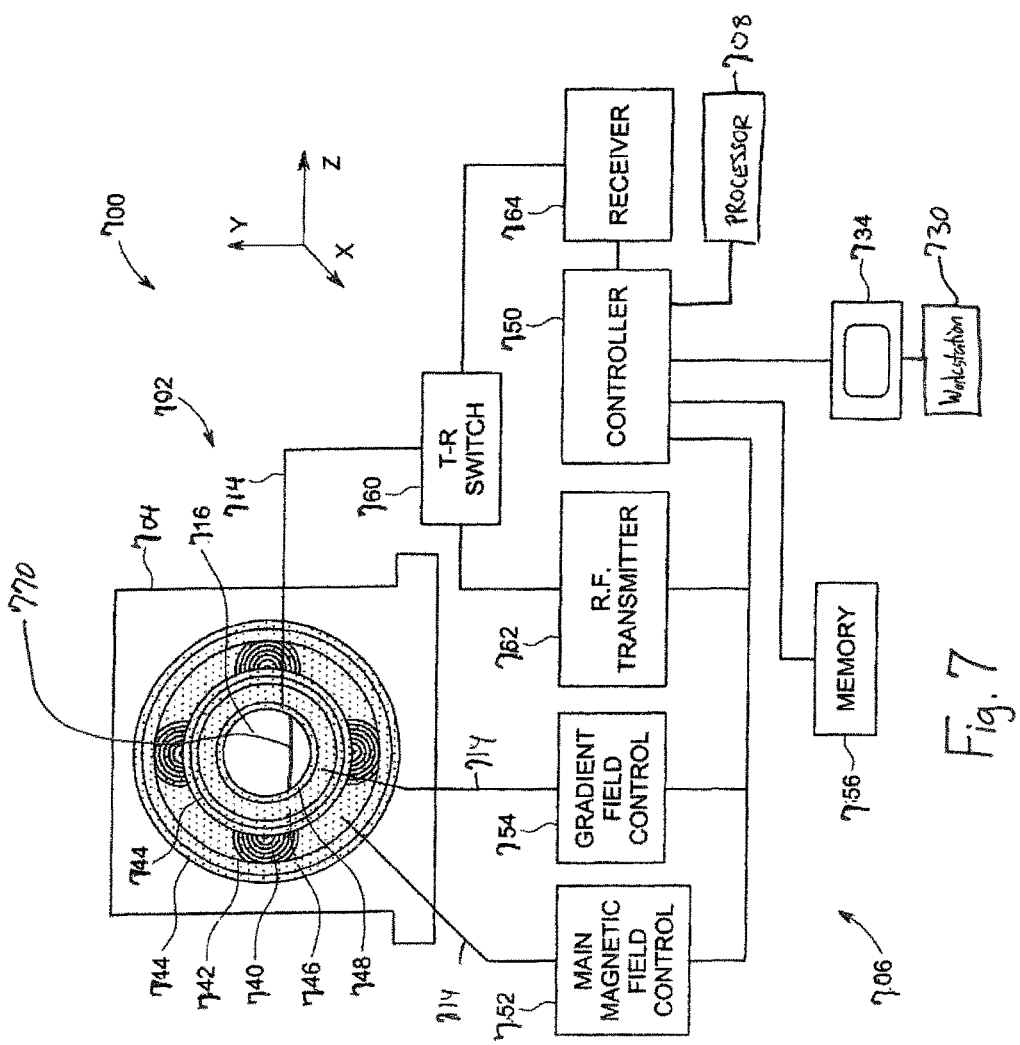
FIG. 7 is a schematic illustration of an exemplary medical imaging system in accordance with various embodiments.

Various embodiments described herein may be provided as part of, or used with, a medical imaging system, such as the imaging system 700 shown in FIG. 7. It should be appreciated that although the imaging system 700 is illustrated as a single modality imaging system, the various embodiments may be implemented in or with multi-modality imaging systems. The imaging system 700 is illustrated as an MRI imaging system. Moreover, the various embodiments are not limited to medical imaging systems for imaging human subjects, but may include veterinary or non-medical systems for imaging non-human objects, luggage, etc. Additionally, the various embodiments may be implemented in connection with non-imaging systems.

Referring to FIG. 7, the imaging system 700 includes an imaging portion 702 having an imaging unit 704 (e.g., imaging scanner) and a processing portion 706 that may include a processor 708 or other computing or controller device. In particular, the imaging unit 704 enables the imaging system 700 to scan an object or patient to acquire image data, which may be image data of all or a portion of the object or patient. The imaging unit 704 includes one or more imaging components that allow acquisition of image data. The imaging components produce signals that represent image data that is communicated to the processing portion 706 via one or communication links 714 that may be wired or wireless. The patient may be positioned within a bore 716 using, for example, a motorized table and then MR imaging performed as described in more detail herein.

In operation, an output of one or more of the imaging components is transmitted to the processing portion 706, and vice versa, which may include transmitting signals to or from the processor through a control interface, which may be embodied as a system interface. The processor 708 also may generate control signals for controlling the position of the motorized table or imaging components based on user inputs or a predetermined scan. For example, RF signals or transmit pulses may be communicated through the one or more communication link 714.

During a scan, image data, such as magnetic resonance image data from the imaging components may be communicated to the processor 708 through a data interface via the control interface, for example, as acquired by a body coil or surface coil, such as the head coil system 100.

The processor 708 and associated hardware and software used to acquire and process data may be collectively referred to as a workstation. The workstation 730 may include, for example, a keyboard and/or other input devices such as a mouse, a pointer, and the like, and a monitor 734. The monitor 734 displays image data and may accept input from a user if a touchscreen is available.

In the exemplary embodiment, the imaging system 700 also includes a superconducting magnet 740 formed from magnetic coils supported on a magnet coil support structure. However, in other embodiments, different types of magnets may be used, such as permanent magnets or electromagnets. A vessel 742 (also referred to as a cryostat) surrounds the superconducting magnet 740 and is filled with liquid helium to cool the coils of the superconducting magnet 740. A thermal insulation 744 is provided surrounding the outer surface of the vessel 742 and the inner surface of the superconducting magnet 740. A plurality of magnetic gradient coils 746 are provided within the superconducting magnet 740 and an RF transmit coil 748 is provided within the plurality of magnetic gradient coils 746. The components within a gantry generally form the imaging portion 702. It should be noted that although the depicted superconducting magnet 740 is a cylindrical shaped, other shapes of magnets can be used.

The processing portion 706 also generally includes a controller 750, a main magnetic field control 752, a gradient field control 754, a memory 756, the display device 734, a transmit-receive (T-R) switch 760, an RF transmitter 762 and a receiver 764.

In operation, a body of an object, such as the patient or a phantom to be imaged, is placed in the bore 716 on a suitable support, for example, a motorized table or other patient table, such as the patient table 770. The superconducting magnet 740 produces a uniform and static main magnetic field $B_o$ across the bore 716. The strength of the electromagnetic field in the bore 716 and correspondingly in the patient, is controlled by the controller 750 via the main magnetic field control 752, which also controls a supply of energizing current to the superconducting magnet 740.

The magnetic gradient coils 746, which include one or more gradient coil elements, are provided so that a magnetic gradient can be imposed on the magnetic field $B_o$ in the bore 716 within the superconducting magnet 740 in any one or more of three orthogonal directions x, y, and z. The magnetic gradient coils 746 are energized by the gradient field control 754 and are also controlled by the controller 750.

The RF transmit coil 748 is arranged to transmit RF magnetic pulses and/or optionally detect MR signals from the patient if receive coil elements are not provided. In various embodiments, the head coil system 100 detects MR signals from the patient. The RF transmit coil 748 and the receive coil(s) are selectably interconnected to one of the RF transmitter 762 or receiver 764, respectively, by the T-R switch 760. The RF transmitter 762 and T-R switch 760 are controlled by the controller 750 such that RF field pulses or signals that are generated by the RF transmitter 762 are selectively applied to the patient for excitation of magnetic resonance in the patient.

Following application of the RF pulses, the T-R switch 760 is again actuated to decouple the RF transmit coil 748 from the RF transmitter 762. The detected MR signals are in turn communicated to the controller 750. The controller 750 includes a processor (e.g., image reconstruction processor), for example the processor 708, that controls the processing of the MR signals to produce signals representative of an image of the patient.

The processed signals representative of the image are also transmitted to the display device 734 to provide a visual display of the image. Specifically, the MR signals fill or form a k-space that is Fourier transformed to obtain a viewable image. The processed signals representative of the image are then transmitted to the display device 734.

Thus, various embodiments provide patient stability during MRI scans of anatomy including a head. Various embodiments also provide for adaptability of equipment for a wide variety of patient head sizes, and/or may provide improved patient comfort, and/or improved image quality, and/or improved safety and/or reduced cost of MRI scans.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A system for magnetic resonance imaging (MRI) of anatomy including a head, the system comprising:
a base member removably mountable to an MRI table, the base member configured to support at least one of an upper body and a head;
a plurality of support members movably fixed to the base member and configured to translate laterally across a width of the MRI table across a surface of the base member, the support members releasably securable to the base member in a plurality of positions along the surface of the base member;
a posterior reception unit fixed in position to the base member, the posterior reception unit configured for abutment with a posterior portion of a human head and comprising at least one radio frequency (RF) receive coil disposed within the posterior reception unit; and
a plurality of articulable reception units movable with respect to the posterior reception unit from an open position to a plurality of closed positions, the articulable reception units mounted physically separately and independently from each other to corresponding support members of the plurality of support members movably fixed to the base member, wherein the open position corresponds to a position wherein a head may be inserted or removed between the articulable reception units, and the plurality of closed positions correspond to a respective plurality of positions wherein the articulable reception units are proximate to a corresponding respective plurality of differently sized heads, each articulable reception unit comprising at least one radio frequency (RF) receive coil disposed within a body, the body configured for abutment with a portion of a head, wherein the plurality of articulable reception units are releasably secured in the plurality of closed positions by at least one of the plurality of support members.

2. A system in accordance with claim 1 wherein the plurality of articulable reception units comprise first and second side reception units, the first and second side reception units joined to the posterior reception unit and disposed on opposing lateral sides of the posterior reception unit, the first and second side reception units pivotable with respect to the posterior reception unit from the open position to the plurality of closed positions.

3. A system in accordance with claim 1 wherein the plurality of reception units comprise first and second side reception units and a crown reception unit, the first and second side reception units laterally opposed and defining a first axis, the crown reception unit configured for abutment to an upper portion of a human head, and wherein the plurality of support members comprise a crown support member, the crown support member movably engaged with the base member, wherein the crown support member translates generally perpendicular to the first axis.

4. A system in accordance with claim 3 wherein the first and second side reception units comprise a plurality of loop coils and the crown reception unit comprises a plurality of saddle coils.

5. A system in accordance with claim 1, wherein the plurality of articulable reception units comprise first and second side reception units, the first and second side reception units separated from the posterior reception unit and disposed on opposing lateral sides of the base member, the first and second side reception units joined to respective first and second side supports and slidable in a generally lateral direction from the open position to the plurality of closed positions.

6. A system in accordance with claim 1, wherein the plurality of articulable reception units comprise first and second side reception units and a crown reception unit, the first and second side reception units and crown reception units joined to the posterior reception unit and pivotable from the open position to the plurality of closed positions, wherein each of the first and second side reception units and crown reception units are supported in the plurality of closed positions by a corresponding at least one of the plurality of support members.

7. A system in accordance with claim 1 further comprising an anterior reception unit and an anterior support member, the anterior support member comprising an arm mounted to and extending away from the base member, the anterior reception unit pivotably connected to the arm and supported at a distance from the base member, the anterior reception unit pivotable from a first position to a second position.

8. A system in accordance with claim 7 wherein the plurality of articulable reception units comprise first and second side reception units laterally opposed to each other, and wherein the anterior reception unit contacts the first and second side reception units in the second position.

9. A system in accordance with claim 1 wherein the plurality of articulable reception units comprise first and second side reception units laterally opposed to each other, and wherein each of the first and second side reception units comprise at least eight loop coils.

10. A system in accordance with claim 1 wherein the plurality of articulable reception units comprise first and second side reception units and first and second crown reception units, the first and second side reception units laterally opposed to each other, the first crown reception unit extending from and pivotable with respect to the first side reception unit, and the second crown reception unit extending from and pivotable with respect to the second side reception unit.

11. A system in accordance with claim 1 wherein the plurality of articulable reception units are independently and continuously adjustable between the plurality of closed positions.

12. A system for magnetic resonance imaging (MRI) of anatomy including a head, the system comprising:
a base member removably mountable to an MRI table, the base member comprising a planar upper surface, the base member configured to support at least one of an upper body and head;
a first side track extending laterally proximate to the upper surface of the base member;
a first side support member movably fixed to the base member, the first side support member extending perpendicularly from the base member and releasably securable to the base member along a length of the first side track, and configured to translate laterally across the upper surface of the base member along a portion of the first side track;
a second side track extending laterally proximate to the upper surface of the base member;
a second side support member laterally opposed to the first side support member and movably fixed to the base member, the second side support member extending perpendicularly from the base member and releasably securable to the base member along a length of the second side track, and configured to translate laterally across the upper surface of the base member along a portion of the second side track;
a first side reception unit movable from an open position to a plurality of closed positions, the first side reception unit comprising a plurality of radio frequency (RF) receive coils disposed within a first side body, the first side body configured for abutment with a side portion of a human head, wherein the first side reception unit is mounted to the first side support member and releasably secured in the plurality of closed positions by the first side support member;
a second side reception unit mounted independently and physically separately from the first side reception unit, the second side reception unit movable from an open position to a plurality of closed positions, the second side reception unit comprising a plurality of RF receive coils disposed within a second side body, the second side body configured for abutment with a side portion of a human head, wherein the second side reception unit is mounted to the second side support member releasably secured in the plurality of closed positions by the second side support member; and
a posterior reception unit fixed in position to the base member, the posterior reception unit configured for abutment with a posterior portion of a human head and comprising at least one radio frequency (RF) receive coil disposed within the posterior reception unit, wherein the first and second side reception units are movable with respect to the posterior reception unit.

13. A system in accordance with claim 12 further comprising:
a crown track extending longitudinally proximate to the upper surface of the base member, the generally longitudinal direction substantially perpendicular to the lateral direction;
a crown support member movably fixed to the base member, the crown support member mounted independently and physically separately from the first side reception unit and the second side reception unit, the crown support member releasably securable to the base member along a length of the crown track, and configured to translate across the upper surface of the base member along a portion of the crown track, wherein the crown support member is configured to translate across the upper surface in a perpendicular direction to a direction translated by the first side support member; and
a crown reception unit movable from an open position to a plurality of closed positions, the crown reception unit comprising a plurality of RF receive coils disposed within a crown body, the crown body configured for abutment with an upper portion of a human head, wherein the crown reception unit is releasably secured in the plurality of closed positions by the crown support member.

14. A system in accordance with claim 13 wherein the first and second side reception units comprise a plurality of loop coils and the crown reception unit comprises a plurality of saddle coils.

15. A system in accordance with claim 12, wherein the first and second reception units are joined to and pivotable with respect to the posterior reception unit.

16. A system in accordance with claim 12 further comprising an anterior reception unit and an anterior support member, the anterior support member comprising an arm mounted to and extending away from the base member, the anterior reception unit pivotably connected to the arm and supported at a distance from the base member, the anterior reception unit pivotable from a first position to a second position.

17. A system in accordance with claim 16 wherein the anterior reception unit contacts the first and second side reception units in the second position.

18. A method for magnetic resonance imaging (MRI) a portion of anatomy including a head, the method comprising:

providing a plurality of articulable reception units, the articulable reception units in an open position when spaced apart to accept a human head within a volume defined by the articulable reception units, each of the plurality of articulable reception units comprising at least one radio frequency (RF) coil, the articulable reception units physically separately mounted from each other;

configuring the plurality of articulable reception units to allow positioning a head of a patient in a desired position for performing an MRI scan and to allow moving the plurality of articulable reception units from the open position to a closed position, wherein the plurality of articulable reception units each abut a portion of the head of the patient, wherein a posterior reception unit is positioned beneath the head of the patient and fixed in position with respect to a base member, the posterior reception unit configured for abutment with a posterior portion of a human head and comprising at least one radio frequency (RF) receive coil disposed within the posterior reception unit; and providing a plurality of support members proximate to the plurality of articulable reception units and configuring the plurality of support members to translate across a surface of the base member to which the plurality of support members are movably mounted, wherein each of the plurality of support members supports at least one of the plurality of articulable reception units in the closed position, and further configuring the plurality of support members to allow movably securing the plurality of support members in place to the base member, wherein the articulable reception units are articulable with respect to the posterior reception unit.

19. A method in accordance with claim 18 wherein the articulable reception units comprise first and second side reception units, and wherein moving the plurality of articulable reception units from the open position to the closed position comprises at least one of bending or pivoting the first and second side reception units with respect to the posterior reception unit.

20. A method in accordance with claim 18 wherein the articulable reception units comprise first and second side reception units, and wherein moving the plurality of articulable reception units from the open position to the closed position comprises sliding first and second side support members associated with the first and second side reception units laterally inwardly.

* * * * *